United States Patent
Vagnoli et al.

(10) Patent No.: US 8,227,595 B2
(45) Date of Patent: Jul. 24, 2012

(54) TAGATOSE PREPARATION

(75) Inventors: Luana Vagnoli, Arezzo (IT); Silvia Giacomelli, Sesio (IT); Marco Manoni, Vinci (IT); Giovanni Cipolletti, Milan (IT)

(73) Assignee: Inalco S.p.A., Milan (IT)

( * ) Notice: Subject to any disclaimer, the term of this patent is extended or adjusted under 35 U.S.C. 154(b) by 253 days.

(21) Appl. No.: 12/661,062

(22) Filed: Mar. 9, 2010

(65) Prior Publication Data

US 2010/0234587 A1    Sep. 16, 2010

(30) Foreign Application Priority Data

Mar. 13, 2009  (IT) .................. FI2009A0048

(51) Int. Cl.
C07H 1/00 (2006.01)
C07H 3/00 (2006.01)
C08B 37/00 (2006.01)

(52) U.S. Cl. ..................................... 536/125

(58) Field of Classification Search ............... None
See application file for complete search history.

(56) References Cited

U.S. PATENT DOCUMENTS

| 5,002,612 A | 3/1991 | Beadle et al. |
| 6,214,124 B1 | 4/2001 | Carobbi et al. |

FOREIGN PATENT DOCUMENTS

| CN | 1985624 | 6/2007 |
| DE | 1939874 | 10/1970 |
| FR | 2862973 | 6/2005 |

OTHER PUBLICATIONS

International Search Report and Written Opinion dated Oct. 7, 2009 for IT FI20090048.

*Primary Examiner* — Layla Bland
(74) *Attorney, Agent, or Firm* — Abelman, Frayne & Schwab

(57) ABSTRACT

The present invention relates to a process for industrially producing tagatose starting from galactose and provides for chemical isomerisation in presence of $XAlO_2$ and XOH (with X=Na, K) and microbiological purification of the residual galactose.

10 Claims, No Drawings

TAGATOSE PREPARATION

FIELD OF THE INVENTION

The present invention relates to the field of preparing ketose sugars from the corresponding aldose sugars, in particular it relates to preparing tagatose from galactose.

BACKGROUND ART

To produce tagatose from galactose two possible approaches are currently known: enzymatic or chemical. For the enzymatic approach, the use of arabinose isomerase is known, while for the chemical approach the use of strong bases is necessary in presence of an agent capable of complexing with tagatose to preserve the structure thereof so that it is not subject to degradation in the highly alkaline environment.

WO 2003/08617 describes the preparation of tagatose through enzymatic isomerisation of galactose mediated by arabinose isomerase with conversions in the order of 40% in around 24 hours; the method also provides for chromatography separation of galactose and tagatose.

WO 2008/072864 describes a method for preparing tagatose from galactose using an enzymatic approach with the use of arabinose isomerase and in presence of borates; the isomerisation reaction, performed at 60° C. and pH 8.5 after 10 hours produces a conversion of 77%.

Processes for producing tagatose using the enzymatic approach have the great advantage of giving rise to selective and therefore "clean" reactions (without degradation products) but by using arabinose isomerase, the natural substrate of which is not galactose, tagatose production takes place with low conversions and long reaction times and therefore with low productivity on an industrial scale. Moreover, the low conversion of galactose to tagatose makes chromatography purification of the latter necessary, a process that is not economically advantageous on an industrial scale.

U.S. Pat. No. 4,273,922 describes isomerisation of galactose to tagatose with a conversion of 52% using a chemical approach in presence of boric acid and a tertiary or quaternary amine in quantities sufficient to produce a pH between 9 and 11 for 6 hours at 70° C. Removal of the residual boric acid at the end of the reaction in however difficult.

WO 92/12263 describes chemical isomerisation of galactose to tagatose; the reaction is performed at pH 12.5 at room temperature for around 2 hours in presence of $Ca(OH)_2$ and $CaCl_2$, thus obtaining conversions of around 85% upon reaching which the reaction is neutralised by $CO_2$ insufflation so as to obtain precipitation of $CaCO_3$, which is removed by filtration.

CN 1985624 describes isomerisation of galactose to tagatose, without the addition of bases, in presence of $NaAlO_2$ at 10-37° C. for 1-3 hours, after cooling the solution is acidified with the addition of $H_2SO_4$ which produces a precipitate containing aluminate which is removed thus providing a tagatose solution.

Prior art processes provide, after isomerisation, a tagatose solution contaminated by albeit small quantities of galactose which are however difficult to remove by crystallisation as galactose is less soluble than tagatose and therefore require purification processes that are not economically advantageous, such as chromatography.

The object of the present invention is to provide a process, which is also applicable on an industrial scale, for preparing tagatose with high degrees of purity, using low cost starting materials, by chemical isomerisation of galactose and by removing residual galactose in an economically advantageous and simple manner that does not require the use of costly and complicated purification techniques.

SUMMARY OF THE INVENTION

The present invention provides a process capable of solving the aforesaid problems. The subject matter of the present invention is a process for producing, also on an industrial scale, tagatose starting from galactose, said process comprising the following steps:
  i) isomerising by chemical approach galactose to tagatose in presence of $XAlO_2$ and XOH wherein X=Na, K;
  iii) removal of residual galactose employing microorganisms which use said galactose as carbon source, leaving unchanged the tagatose.

The aforesaid method is economically advantageous and allows crystalline tagatose with a HPLC purity >98% and high yields to be obtained.

The use of microorganisms allows complete removal of residual galactose and this step is essential to obtain tagatose with high purity.

The process uses low cost raw materials and, moreover, the quantitatively precipitated and removed aluminium salts can be recycled, in a particularly advantageous way when X=K.

Recycling of the aluminium salts has the great advantage of drastically decreasing processing waste, which moreover has a low environmental impact.

DETAILED DESCRIPTION OF THE INVENTION

The present invention relates to a process for preparing tagatose starting from galactose, said process comprising the following steps:
  i) isomerising by chemical approach galactose to tagatose in presence of $XalO_2$ and XOH wherein X=Na, K;
  iii) removal of residual galactose employing microorganisms which use said galactose as carbon source, leaving unchanged the tagatose.

According to a preferred aspect, said process comprises after step (i) the following step:
  ii) acidifying the reaction mixture in such a way to obtain the quantitative precipitation of aluminium salts which are removed to obtain a solution enriched in tagatose.

According to a preferred aspect, said process comprises after step (iii) the following step:
  iv) isolating tagatose from the enriched solution obtained from step (iii).

The possibility of producing tagatose (D or L) in an economically viable way is linked to the availability of a low cost galactose source (D or L). The best source of galactose is lactose, in crystal or in solution, from which a mixture of glucose and galactose is obtained by acid or enzymatic hydrolysis, from which the glucose is removed by crystallisation, by chromatography or by another method. Galactose can be also be obtained from lactose using fermentation processes (for example as described in WO2005039299).

Therefore, advantageously, as starting material for the present process galactose with a degree of purity of at least 70% can be used and therefore galactose with low purity as obtained from lactose using known processes can also be used. For example, in a particularly advantageous manner, crystalline galactose, or directly the solution deriving from fermentation processes as described in WO2005039299, can be used.

In step (i) in presence of $XAlO_2$ in $XOH$ isomerising galactose to tagatose is performed with high conversion percentages by forming of a stable tagatose-aluminate complex.

Preferably X=K.

The reagent that produces the isomerisation reaction is a solution of $XAlO_2$ in $XOH$ characterized by pH >12. To minimise the costs of the starting material, rather than purchasing $XAlO_2$ it is less expensive to prepare it starting from $Al(OH)_3$ and $XOH$ in water under reflux, in suitable concentrations and mutual ratios. Preferably, the molar ratio aluminate/free base ($AlO_2^-/OH^-$) is comprised between 0.65 and 2.0, more preferably between 1.0 and 2.0.

The isomerising step of galactose to tagatose takes place in solution, in presence of solutions of $XAlO_2$ in $XOH$: the conversion proceeds with molar conversion percentages of galactose to tagatose of over 85%, preferably over 90%. The isomerising step is performed at temperatures comprised between 30 and 50° C., preferably comprised between 34 and 40° C., for times comprised between 5 and 25 hours, preferably between 8 and 20 hours, more preferably between 9 and 11 hours. The driving force of isomerisation is the formation of a stable tagatose-aluminate complex which remains in solution in the reaction mixture, and which preserves the product from degradation in alkaline environment to which carbohydrates are instead normally subjected. Working with $KAlO_2$ or with $NaAlO_2$ at the same conditions produces identical isomerisations both as conversion percentages and as HPLC profile of the products formed.

When, through HPLC control, the conversion percentage from galactose to tagatose is greater than 85%, preferably greater than 90%, isomerisation is stopped and the reaction mixture stabilised, by acidification to pH below 6, preferably below 4. Acidification is typically exothermic and it is preferable to control the temperature of the mixture so that it does not exceed 50° C. Any acid can be used for acidification: clearly, it is advantageous to use acids available at low cost and simple to handle that form insoluble aluminium salts, which can therefore be removed by simple filtration. By way of example, $H_2SO_4$, $HNO_3$, $H_3PO_4$, acetic acid, formic acid, lactic acid, citric acid can be used for acidification; preferably $H_2SO_4$ at 20-50% is used. The acidification step is delicate as by acidifying the reaction mixture in such a way as to pass gradually from pH>12 to pH comprised between 6 and 7, $Al(OH)_3$ precipitation occurs, forming a dense, colloidal precipitate, extremely difficult to filter and which also makes the mixture difficult to stir and to handle and, after this dense precipitate has formed, although further decreasing the pH, it is almost impossible to transform it into a more easily filtered precipitate.

In the case in which $KAlO_2$ and $KOH$ are used for isomerisation, it is convenient to acidify the reaction mixture transferring it on an aqueous solution of $H_2SO_4$ at 20-50% so as to obtain a mixture in which the pH is below 3; this produces direct and quantitative precipitation of $KAl(SO_4)_2$ which can be easily removed by filtration.

In the case in which $NaAlO_2$ and $NaOH$ are used for isomerisation, it is advantageous to acidify the reaction mixture transferring it on an aqueous solution of $H_2SO_4$ at 20-50% so as to obtain a mixture in which the pH is below 4; in this case no direct precipitation of aluminium salts is produced, but by basifying the mixture to pH comprised between 5.5 and 7.5 with $Ca(OH)_2$ it is possible to obtain precipitation of a mixed salt of $Al(OH)_3$ and $CaSO_4$ which is easily removed by filtration.

After quantitative precipitation of the aluminium salts the solution is purified, to remove the residual galactose, employing microorganisms that use said residual galactose as carbon source, leaving unchanged the tagatose. Microbiological purification of the solution, which is preferably performed at 30-40° C. for 12-24 hours, is, just as isomerisation, a critical step of the process, as complete removal of galactose is essential to allow direct tagatose crystallisation with high yields and high purity.

For microbiological purification it is preferable to use microorganisms comprising one of more species of genus *Saccharomyces*, more preferably common baking yeast (i.e. *Saccharomyces cerevisiae*).

To proceed with microbiological purification the solution obtained from step (i) must be taken to an osmotic value adequate for survival of the microorganisms, or to a conductivity <30 mS/cm. Said conductivity is preferably obtained by dilution with water.

After microbiological purification, tagatose is isolated, preferably by steps of demineralising on ion exchange resins, microfiltering, concentrating and crystallising from water or water/solvent.

The aluminium salts recovered can be used to again produce the initial catalyst by simple resuspension in appropriate quantities of strong base: the species $XAlO_2$ in $XOH$ will therefore be reformed. In this way, the processing waste is reduced to salts with low environmental impact whose disposal will have little impact on process costs. Recovery of the insoluble aluminium salts is particularly simple and advantageous in the case in which X=K and the isomerisation mixture has been acidified with $H_2SO_4$.

The present invention may be better understood in light of the following examples.

EXPERIMENTAL PART

Example 1

200 g of galactose (1.1 moles) is suspended in 160 ml of water and, under gentle stirring, brought to a temperature of 34° C. 400 g of $KAlO_2$ solution at 25% (1.0 mole) in KOH at 14% (1.0 mole) is added to the galactose solution. The reaction is followed via HPLC and after 20 hours a conversion of 90% is detected.

The isomerised product is transferred to another vessel while sulphuric acid 20% is simultaneously added, transfer and addition are performed at such a speed that the pH of the mixture always remains below 3 and the temperature does not exceed 50° C.: the mixed aluminium and potassium salt that precipitates is filtered off. For acidification of the reaction mixture 1250 g of sulphuric acid 20% is used.

The filtered solution is diluted until reaching conductivity <30 mS/cm, brought to a temperature of 37° C. and returned to neutral pH, and 5 g of baking yeast is then added. The reaction is followed via HPLC and after 24 hours disappearance of galactose is achieved.

The mixture is deionised on strong cationic (AMBERLITE C-200 H$^+$ form) and weak anionic (IRA-96 free base form) ion exchange resin pairs placed in series. The deionised solution is concentrated under vacuum until obtaining 200 g of syrup to which 200 ml of methanol is added. The mixture is heated to 50° C. under stirring to dissolve the syrup in the solvent and then cooled to 10-15° C. to crystallise the tagatose.

After 48 hours the solid is filtered under vacuum and washed with a mixture of water/methanol=1/4. Once dried the solid weighs 98 g, with a yield of 49% based on the starting galactose.

The isolated tagatose has HPLC purity >98%.

Example 2

77 kg of aluminium hydroxide at 94% (0.93 Kmoles) is added to 185 kg of NaOH 30% (1.4 Kmoles): this is maintained under reflux for 2 hours.

The solution of sodium aluminate in soda thus obtained is added after cooling to room temperature to 550 kg of galactose solution at 32% (0.89 moles) brought to a temperature of 40° C.: after 8 hours the reaction is finished with a conversion of 80%

The solution of isomerised product is transferred on 200 L of sulphuric acid 50% checking that the pH always remains below 4. The acidified solution is taken to pH 6.0÷7.0 by adding 500 l of aqueous solution of $Ca(OH)_2$ at 10%. The aluminium and calcium salts that precipitate are filtered off before proceeding with galactose removal.

3.5 kg of baking yeast in blocks is added to the solution desalted on strong cationic (AMBERLITE FPC22 $H^+$ form) and weak anionic (FPA55 free base form) ion exchange resin to obtain conductivity <30 mS/cm and brought to a temperature of 37° C.: after 24 hours disappearance of galactose is obtained.

A portion of the degalactosylated solution is treated as in Example 4.

Example 3

4 kg of galactose (22.2 moles) is suspended in 2.6 kg of $H_2O$ and brought to a temperature of 38° C.

3.96 kg of $KAlO_2$ 44% (17.7 moles) in 13% free KOH (9.2 moles) is added: after 14 hours the reaction is finished with a conversion of 92.5%.

The solution of isomerised product is transferred on sulphuric acid 38% (9.26 kg) checking that the pH always remains below 3: the mixed aluminium and potassium salt that precipitates is filtered off.

The solution deionised by electrodialysis to obtain conductivity <4 mS/cm is brought to a temperature of 37° C. and returned to pH 7.0 with $NH_3$ 22% (35 ml), 100 g of brewer's yeast is added. The reaction is followed by HPLC and after 24 hours complete disappearance of galactose is obtained. The solution is then pasteurised at 70° C. for 1 hour.

The solution is deionised on strong cationic (AMBERLITE FPC22 $H^+$ form) and weak anionic (FPA55 free base form) ion exchange resin pairs placed in series, until obtaining conductivity of the eluate <30 μS/cm.

The solution is concentrated under vacuum to 3.5 kg of syrup and 3.6 l of methanol is added. The mixture is heated to 50° C. under stirring to dissolve the syrup in the solvent and then left to cool first spontaneously to room temperature and then in ice bath to an internal temperature of 10° C. to crystallise the tagatose. After 72 hours the solid is filtered under vacuum and washed with a water/methanol mixture. Once dried the crystalline tagatose weighs 1300 g and has HPLC purity >98%.

The mother liquor is reconcentrated to 1.6 kg and crystallisation is performed as described above adding 1.6 l of methanol. The mixture is heated under stirring to dissolve the syrup in the solvent and then cooled to crystallise the tagatose.

After 72 hours the solid is filtered under vacuum and washed with a water/methanol mixture. Once dried the crystalline tagatose weighs 280 g and has HPLC purity >98%.

Example 4

Tagatose Crystallisation with $NaAlO_2$ 150 l tagatose solution at 13.2% obtained by epimerisation with $NaAlO_2$ (see Example 2) is concentrated under vacuum to 50%.

The solution is brought to a temperature of 40° C. and triggered with 200 g of crystalline tagatose, a crystallisation ramp is performed obtained by cooling in 6 days until reaching 5° C.

The crystalline suspension is centrifuged obtaining 10.1 kg of crystalline tagatose with HPLC purity >98%, while 9.8 kg of tagatose are found in the mother liquor: Crystallisation yield=51%.

Example 5

Epimerisation with Recycled $KAlO_2$ 500 g of $KAlO_2$ 14.7% (0.75 moles) in KOH at 5% (0.45 moles), prepared recycling the mixed aluminium and potassium salt, obtained by an epimerisation reaction (as in Example 1), by treatment with a 50% KOH solution, is added to 400 g of galactose solution at 32% (0.71 moles) brought to a temperature of 40° C. After 11 hours the reaction is finished with a conversion of 86% and chromatography profile identical to the reactions deriving from isomerisation with freshly prepared aluminate.

The steps subsequent to conversion to tagatose follow those of the epimerisation reaction obtained with freshly prepared aluminate.

Example 6

Tagatose Preparation According to the Description in CN 1985624 Example 1 Using Home Made $NaAlO_2$ 5 g of galactose is dissolved in 45 ml of $H_2O$ and brought to a temperature of 25° C.

4.5 ml of $H_2O$ is added to 2.5 g of $NaAlO_2$ deriving from calcination of mixed sodium/aluminium carbonate salt with formula type $NaAl(OH)_3HCO_3$: the salt remains in suspension and the $NaAlO_2$ suspension is added to the galactose solution: after monitoring by HPLC for 1 hour and 30 minutes the presence of galactose and absence of tagatose is still detected; after 20 hours galactose is still present and tagatose absent.

Example 7

Tagatose Preparation According to the Description in CN 1985624 Examples 1 and 2 Using Commercial $NaAlO_2$ A: 50 g of galactose (0.277 moles) is solubilised in 450 ml of $H_2O$ and brought to a temperature of 20° C.

25 g of $NaAlO_2$ Riedel-de-Haen Batch 80570 (0.277 moles) is solubilised in 45 ml of $H_2O$ and added to the galactose solution: after monitoring by HPLC for 2 hours the presence of galactose and absence of tagatose is still detected. The temperature is taken to 37° C.: after monitoring by HPLC for another 3 hours a galactose/tagatose ratio=13/87 is detected. After a further 12 hours at 20° C. and 6 hours at 37° C. (23 total hours) a galactose/tagatose ratio=40/60 is still observed.

B: 50 g galactose (0.277 moles) is suspended in 200 ml of $H_2O$ and brought to a temperature of 20° C.

12.5 g of $NaAlO_2$ Riedel-de-Haen Batch 80570 (0.13 moles) is solubilised in 25 ml of $H_2O$ and added to the galactose solution: after monitoring by HPLC for 2 hours the presence of galactose and absence of tagatose is still detected. The temperature is taken to 37° C.: after monitoring by HPLC for another 3 hours a galactose/tagatose ratio=11/89 is detected. After a further 12 hours at 20° C. and 20 hours at 37° C. (37 total hours) a galactose/tagatose ratio=45/55 is still observed.

The invention claimed is:

1. A process for preparing tagatose starting from galactose, said process comprising the following steps:
   i) isomerising by chemical approach galactose to tagatose in aqueous solution at pH >12 in presence of $XAlO_2$ and XOH wherein X=Na, K;
   iii) removing of residual galactose employing microorganisms which use said galactose as carbon source, leaving unchanged the tagatose to obtain a solution enriched in tagatose.

2. Process according to claim 1 comprising after the step (i) the following step:
   ii) acidifying the reaction mixture in such a way to obtain the quantitative precipitation of aluminium salts which are removed.

3. Process according to claim 1 comprising after the step (iii) the following step:
   iv) isolating tagatose from the enriched solution obtained from step (iii).

4. Process according to claim 1 wherein the molar ratio aluminate/free base ($AlO_2^-/OH^-$) is comprised between 0.65 and 2.0.

5. Process according to claim 4 wherein X=K.

6. Process according to claim 1 wherein said microorganisms comprise one or more species of genus *Saccharomyces*.

7. Process according to claim 6 wherein the removal of galactose (iii) is performed at 30-40° C. for 12-24 hours.

8. Process according to claim 2 wherein the reaction mixture is acidified at a pH below 6 employing an acid chosen in the group $H_2SO_4$, $HNO_3$, $H_3PO_4$, acetic acid, formic acid, lactic acid and citric acid.

9. Process according to claim 3 wherein isolating tagatose (iv) is performed by steps of demineralising on ion exchange resins, microfiltering, concentrating and crystallising from water or water/solvent.

10. A process for preparing tagatose starting from galactose, said process comprising the following steps:
    i) isomerising by chemical approach galactose to tagatose in aqueous solution at pH>12 in presence of $XAlO_2$ and XOH wherein X=Na, K;
    iii) removing of residual galactose employing microorganisms which use said galactose as carbon source, leaving unchanged the tagatose to obtain a solution enriched in tagatose wherein the $XAlO_2$ and XOH to be used are prepared, by treatment with an appropriate amount of a strong base, from the aluminium salts resulting from step (ii) according to claim 2.

* * * * *